United States Patent [19]

Turner et al.

[11] Patent Number: 5,400,808

[45] Date of Patent: * Mar. 28, 1995

[54] NICOTINE-IMPERMEABLE CONTAINER AND METHOD OF FABRICATING THE SAME

[75] Inventors: James E. Turner, Atascosa; Michael P. Ellis; Ronald G. Oldham, both of San Antonio, all of Tex.; Ira Hill, Locust, N.J.; Bengt E. Malmborg, Helsingborg; Sven-Börje Andersson, Ödåkra, both of Sweden

[73] Assignee: Pharmacia Biosystems Aktiebolag, Sweden

[*] Notice: The portion of the term of this patent subsequent to Dec. 1, 2009 has been disclaimed.

[21] Appl. No.: 982,240

[22] Filed: Nov. 25, 1992

Related U.S. Application Data

[63] Continuation of Ser. No. 535,967, Jun. 8, 1990, Pat. No. 5,167,242.

[51] Int. Cl.[6] ............................................. A24F 47/00
[52] U.S. Cl. ...................................... 131/270; 131/273; 131/337; 128/202.21; 128/203.21; 128/203.23; 128/204.13
[58] Field of Search ............... 131/329, 112, 336, 337, 131/335, 359, 270, 273; 128/200.14, 200.19, 200.21, 202.21, 203.12, 203.15, 203.21, 203.23, 204.11, 204.13; 206/242, 438, 484, 524.1, 532, 828; 428/35.2, 35.4

[56] References Cited

U.S. PATENT DOCUMENTS

| | | | |
|---|---|---|---|
| D. 112,952 | 2/1938 | Steiner | 131/329 X |
| 2,860,638 | 11/1958 | Bartolomeo | 131/273 X |
| 4,137,914 | 2/1979 | Wetterlin | 128/200.23 |
| 4,265,948 | 5/1981 | Hayes et al. | 222/92 |
| 4,736,755 | 4/1988 | Oldham et al. | 131/270 |
| 4,800,903 | 1/1989 | Ray et al. | 131/270 X |
| 4,839,174 | 6/1989 | Baker et al. | 131/270 X |
| 4,856,649 | 8/1989 | Inoue | 206/484 X |
| 4,920,989 | 5/1990 | Rose et al. | 131/270 |
| 5,008,110 | 4/1991 | Benecke et al. | |
| 5,016,652 | 5/1991 | Rose et al. | 131/270 |
| 5,077,104 | 12/1991 | Hunt et al. | |
| 5,097,956 | 3/1992 | Davis | 206/484 X |
| 5,167,242 | 12/1992 | Turner et al. | 131/273 |

OTHER PUBLICATIONS

*The Condensed Chemical Dictionary*, 1991, p. 727.

*Primary Examiner*—Jennifer Bahr
*Attorney, Agent, or Firm*—Pravel, Hewitt, Kimball & Krieger

[57] ABSTRACT

The present invention relates to a nicotine-impermeable container including a barrier layer of acrylonitrile and methyl acrylate and a method for fabricating same. Additionally, the invention relates to a nicotine inhaling device which allows a user to ingest nicotine vapors orally. The nicotine inhaling device of the present invention is primarily directed to a device which can be used as a smoking cessation aid.

13 Claims, 2 Drawing Sheets

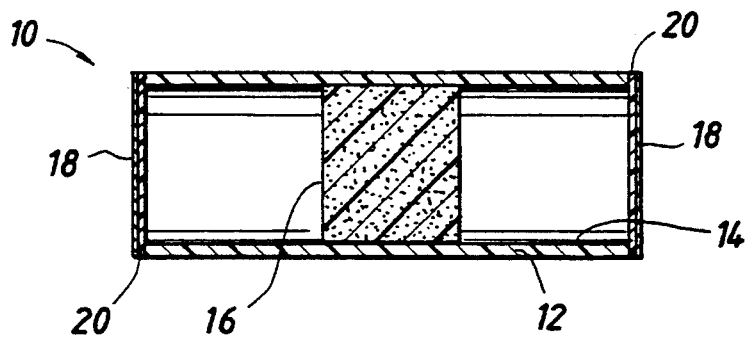
FIG. 1
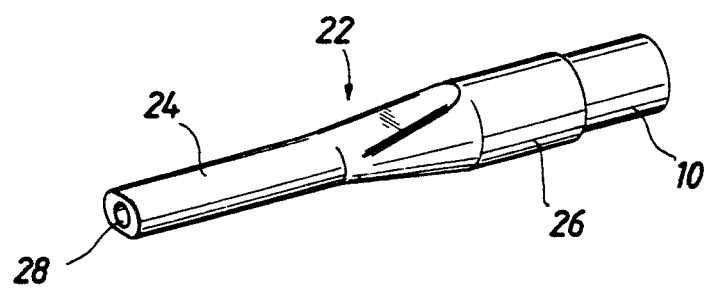
FIG. 2
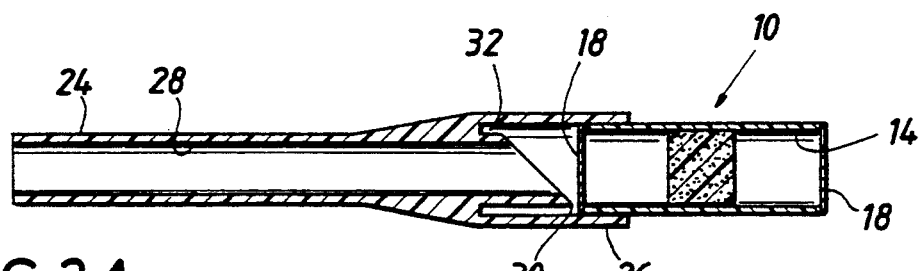
FIG. 3A
FIG. 3
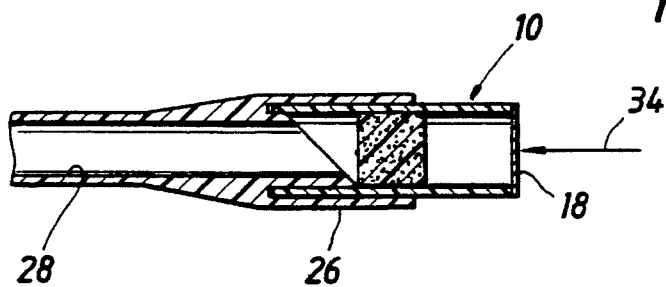
FIG. 3B
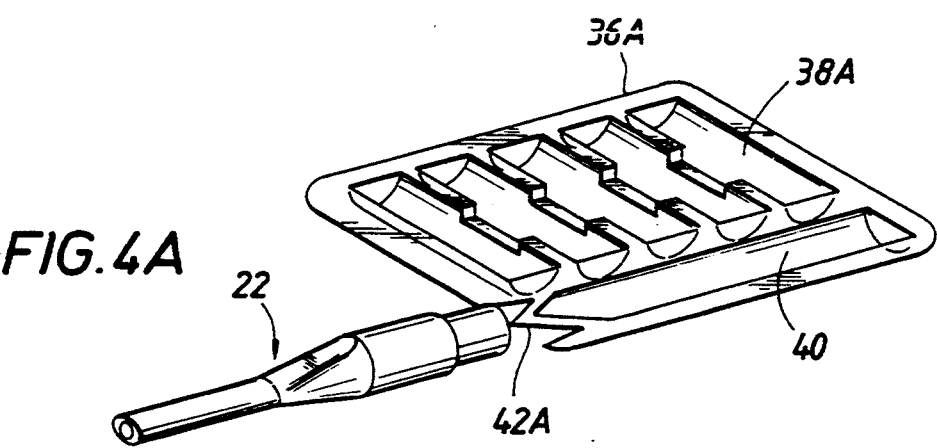
FIG. 4A

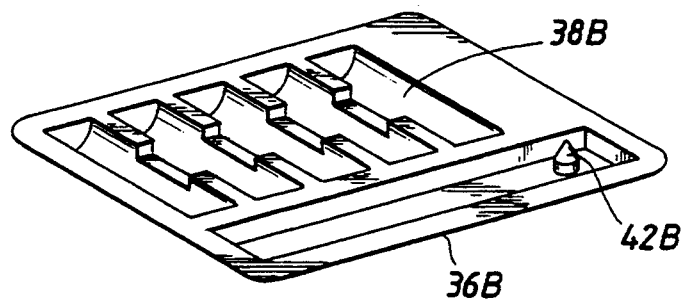
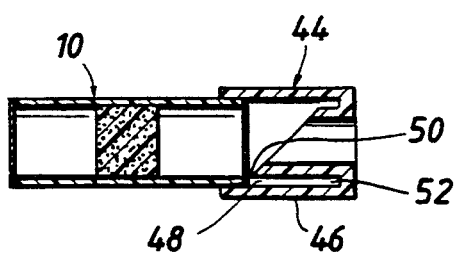
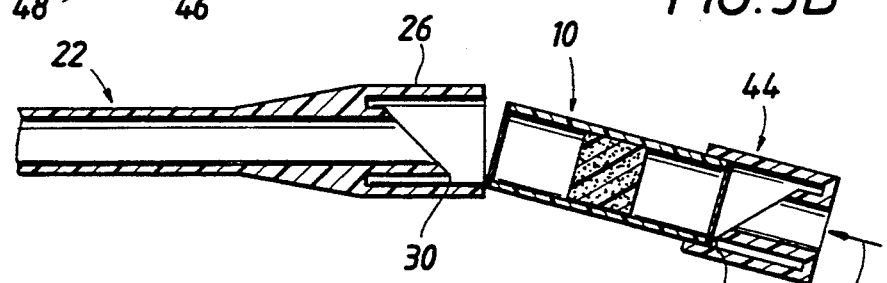
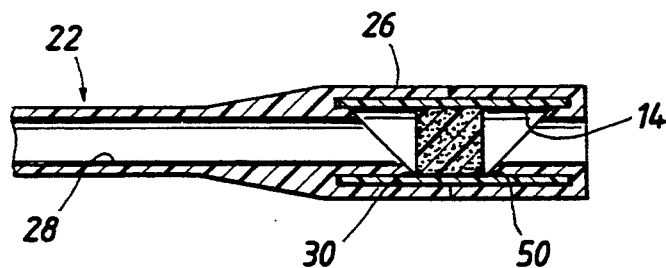
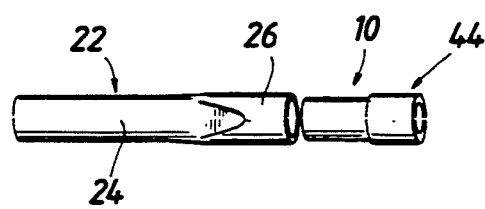
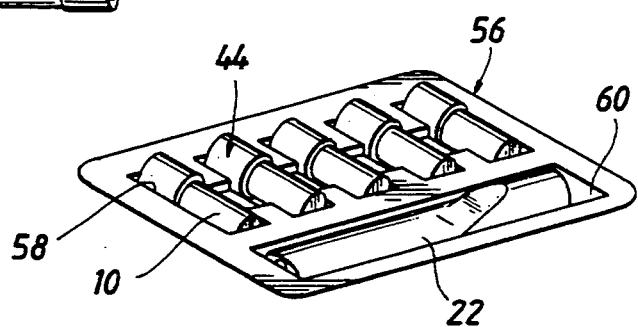

– –

NICOTINE-IMPERMEABLE CONTAINER AND METHOD OF FABRICATING THE SAME

This is a continuation of application Ser. No. 07/535,967, filed Jun. 8, 1990, now U.S. Pat. No. 5,167,242.

FIELD OF THE INVENTION

The present invention relates to a nicotine-impermeable container and a method for fabricating same. A preferred embodiment of the invention is a nicotine inhaling device which allows a user to ingest nicotine vapors orally and is primarily used as a smoking cessation aid.

BACKGROUND OF THE INVENTION

Evidence has been mounting over the years linking many diseases such as high blood pressure and lung cancer to cigarette smoking. The U.S. Surgeon General's report of 1988 on the health consequences of smoking estimated that in the United States alone about 300,000 deaths are caused each year by cigarette-related diseases. Indeed, excessive smoking is now recognized as one of the major health problems throughout the world.

Because of the addictive nature of nicotine, it is extremely difficult for a heavy smoker to stop smoking completely. Even though nicotine is one of the risk factors in tobacco smoke, other substances formed during the combustion of tobacco such as carbon monoxide, tar products, aldehydes and hydrocyanic acid are considered to be even greater risk factors.

Because of the addictive nature of nicotine, an acceptable alternative to smoking has been to provide nicotine in a form or manner other than by smoking. Several products have been developed that accomplish this result. The most successful product which is used as a smoking substitute and/or a smoking cessation aid is a chewing gum known as Nicorette ® which contains nicotine as one of its active ingredients. This product is the only form of nicotine replacement which has been approved by the Food and Drug Administration to date.

In this chewing gum, nicotine is present in the form of a complex with an insoluble cation-exchanger (polacrilex) which is disbursed in a gum base. A buffering agent is included in this composition. U.S. Pat. Nos. 3,877,486; 3,901,248; and 3,845,217 are directed to this product.

Another product generally developed in this field is a smokeless cigarette sold under the trademark Favor which was on the United States market for about 18 months. This product was subsequently withdrawn because it did not satisfy the Food and Drug Administration requirements. Various embodiments of this product are described in U.S. Pat. Nos. 4,284,089; 4,800,903; and 4,813,437.

This product generally allows nicotine to be inhaled through an elongated tube in which a porous polymer reservoir containing nicotine free base is mounted. An air stream caused by suction from the user carries nicotine vapors into the lungs of the user to satisfy a nicotine craving.

In commercial embodiments of this product, the tube was formed of polybutyleneterephtalate (PBTP) and polyethylene (PE) polymers. This tube was wrapped in a polyehtyleneterephthalate (PET) wrapper in order to seal the nicotine from the atmosphere. However, it was unexpectedly found that the nicotine free base migrated through the packaging material and rapidly disappeared from the system because the material was more permeable than anticipated. It has been estimated that the shelf-life of the unrefrigerated vapor inhaler was approximately one month.

The present invention concerns an improvement of the container for holding the nicotine free base, thereby improving the shelf-life and purity of the nicotine stored.

SUMMARY OF THE INVENTION

In order to solve the problems discussed above, in a preferred embodiment of the invention, a container in the form of a cartridge for a nicotine inhaler includes a cartridge housing and a passageway in the housing in which a nicotine reservoir is located. The reservoir is designed to hold a measured amount of nicotine in a form that will allow nicotine vapor to be released into a fluid stream passing around or through the reservoir. The passageway has at least two openings communicating outside the housing for allowing a fluid stream through the passageway. The reservoir is sealed from the atmosphere by a nicotine-impermeable barrier which includes passageway barrier portions for sealing the passageway on both sides of the reservoir with at least these barrier portions being penetrable for opening the passageway to the atmosphere.

In the embodiment of the invention in which the cartridge is a cylinder, the passageway is defined by the inner surface of the cylinder with openings at both ends. The nicotine reservoir can be in the form of a polymer plug in which a nicotine free base is applied. In order to seal the reservoir from the atmosphere, the tube or cylinder can be formed of a material that is impermeable to oxygen, nitrogen and nicotine, such as a copolymer of acrylonitrile and methyl acrylate. An example of this material is manufactured by B.P.-Sohio under the trade name Barex. Aluminium foil coated with Barex could also be used.

The openings in the cylinder are sealed by a thin aluminum foil or other type of flexible, penetrable, material that is impermeable to oxygen, nitrogen and nicotine. In order to provide an easy means for sealing the aluminum foil to the ends of the cylinder, the foil can be coated on its inner surface with a thin layer or film of Barex and the composite can be heat sealed to the ends of the cylinder for forming the passageway barrier portions.

In order to protect the nicotine in the reservoir from degrading in the presence of oxygen, the reservoir can be inserted in the tube in an oxygen-free environment and filled with an inert gas such as nitrogen. One way of accomplishing this result is to load the nicotine reservoir in the tube in a nitrogen atmosphere and then sealing the Barex-covered aluminum foil pieces to the ends of the tube. Barex and aluminum have been chosen as the materials to use because they exhibited negligible penetration of nicotine during the shelf-life period and Barex is a good heat sealing material.

When the inhaler is ready to be used, it can be placed in a specially designed mouthpiece which has a receiving end surrounding the passageway with a sharp tip adjacent the passageway in the mouthpiece for penetrating one end of the cylinder when it is inserted into the receiving end. The other end of the cylinder can be penetrated by any suitable means such as, for example, a sharp object in the form of a knife or a holder especially designed to fit over the other end of the tube with a sharpened tip around an opening that leads to the atmosphere. After the cartridge is inserted into the mouthpiece and both ends are penetrated, the user is able to suck on the mouthpiece and receive a satisfactory dose of nicotine vapor to satisfy his or her craving.

The cartridges can be sold in dispensing kits containing a number of cartridges along with a single mouthpiece. In the embodiment where the outer end of the cartridge needs to be penetrated by an object other than a part of the inhaler, the dispensing container can include a sharpened edge for easy use.

The invention can be applied to other embodiments where nicotine needs to be stored, in a container which provides easy access to the user, for long periods of time before it is used.

In order to receive a complete understanding of the invention, the detailed description of exemplary embodiments set forth below should be considered in conjunction with the accompanying drawings, in which:

FIG. 1 is a sectional view of a cartridge of the present invention in which a nicotine reservoir is located;

FIG. 2 is a perspective view of the cartridge of FIG. 1 inserted into a mouthpiece;

FIG. 3 is a sectional view of the cartridge of FIG. 1 in the end of the mouthpiece of FIG. 2, FIG. 3A showing the cartridge ready to be inserted to penetrate the foil at one end of the cartridge, and FIG. 3B showing the cartridge fully inserted into the mouthpiece;

FIGS. 4A-B are perspective views of a dispensing kit with a sharpened edge for the cartridge and mouthpiece shown in FIGS. 1-3;

FIGS. 5A-C are sectional views that show the cartridge of FIG. 1 being inserted into a mouthpiece with the outer end being penetrated by an outer end cap portion of the mouthpiece;

FIG. 6 is a perspective view of the embodiment shown in FIG. 5; and

FIG. 7 is a perspective view of a dispensing kit of the embodiment of the invention shown in FIGS. 5 and 6.

DETAILED DESCRIPTION OF EXEMPLARY EMBODIMENTS

Referring to the drawings, exemplary embodiments of the invention will be described in detail. FIG. 1 shows cartridge 10, in accordance with the invention, which is formed of a cylindrical body 12 that defines a passageway 14 through which a stream of fluid such as air can travel. A reservoir 16 is mounted within the passageway 14 for holding nicotine free base for the reasons discussed below. The reservoir 16 can be formed of a porous polymer plug or other suitable materials such as described in U.S. Pat. Nos. 4,284,089; 4,800,903; and 4,813,437, the contents of such patents being incorporated by reference as though fully set forth herein. These three patents are now owned by the entity which owns the invention described in this patent application.

For the purposes of the invention as described, the reservoir is formed of porous polyethylene in which a thin layer of liquid nicotine has been distributed. Details of the porous plug and its operation and the composition of nicotine are described in greater detail in U.S. Pat. No. 4,800,903.

For the purposes of this invention, the polyethylene plug can be charged with a mixture of nicotine, menthol, and ethanol. The weight ratio of nicotine to menthol to ethanol is preferably about 10:1:120. A weight ratio of 10:1:160 has additionally been tested and proved to function well. As an example, the composition of the loading solution for approximately 150,000 polyethylene plugs is made up of 18,000 grams of ethanol, 1,500 grams of nicotine, and 150 menthol. A given amount of ethanol is placed in a mixing vessel (not shown) and the menthol is added and stirred until it is completely dissolved.

Nicotine is then added through the solution and agitated manually for about three minutes. A tight fitting lid is then placed on the mixing vessel. The temperature of cooling water in a condenser (not shown) is then adjusted to 14° C. and circulated at a volume of 10 liters/minute. A jacketed vacuum drier (not shown), with an inner volume of 260 liters, has water circulated through the jacket at a temperature of 20°±1° C. at a volume of 5 liters/minute. The plugs are placed into the vacuum drier and the vessel is evacuated to less than −27 inches of mercury.

The nicotine/ethanol solution is sucked by the aid of the under pressure into the vacuum drier. The vacuum valve is then shut. The vacuum should be less than 20 inches of mercury. The vacuum drier is then rotated at a speed of 4 revolutions per minute for 10 minutes. The vacuum pump is then started and vacuum valve opened and the temperature on the inlet water to the vacuum drier is raised to 40°±1° C. The vacuum drier and pump should operate until a temperature differential of 5°-6° is reached between the inner temperature of the vacuum drier and the inlet water to the same drier. A Kinney High Vacuum Pump Model KC-8 was utilized in the above-described procedure.

When the temperature differential mentioned above is reached, the vacuum drier and pumps are stopped. The vacuum drier is then filled with nitrogen and the polyethylene plugs are unloaded into a specially designed container which is evacuated to a pressure of minus 28 inches of mercury and then refilled with nitrogen. This procedure is then repeated to make sure all of the oxygen has been removed from the system. The nitrogen-loaded polyethylene plugs are then kept in a bulk container filled with nitrogen to protect the nicotine against oxygen. The plugs are then inserted into suitable tubes in a nitrogen atmosphere and sealed as discussed below.

In order to prevent oxygen from migrating into the cartridge 10 after it is fabricated and to prevent the nicotine from migrating out of the cartridge 10, the cylindrical body 12 is formed of a nicotine-impermeable material. A suitable material found for this purpose is a copolymer of acrylonitrile and methacrylate sold under the trade name Barex ® by B.P.-Sohio.

A variety of compounds had been tested for use as nicotine-impermeable materials. Initially, it was believed that crystalline polymers, due to the small nature of their interstitial spaces, would make good candidates. However these compounds were found to be ineffective in deterring nicotine migration. Unexpectedly, Barex proved to be an effective material even though it is an amorphous polymer.

Barex is particularly suited to the application described since it is heat sealable to provide a nicotine-impermeable barrier at the seal and is composed of ingredients which are permissible for use as an adhesive under the provisions of F.D.A. Regulation 21 CFR 175.105. Barex can also be adhered to aluminum or other metal foils so that a suitable nicotine-impermeable package can easily be formed by heat sealing adjacent layers of Barex film with the aluminum foil as a backing for one or more layers.

For the embodiment of FIG. 1, in order to maintain the inert gas in the tube after the reservoir 16 has been inserted, both ends of the tube are covered with a nicotine-impermeable barrier such as a layer of aluminum foil 18. The foil layers are sealed to the Barex tube 12 through a layer of Barex 20 adhered to the foil 18 so that the layers of foil 18 can easily be sealed to the ends of the Barex tube 12 through the application of heat. While the Barex is adhered to the aluminum foil by the use of a suitable adhesive, such adhesives cannot be used to seal the layers of Barex together or the aluminum foil to the Barex since such adhesives are not themselves nicotine-impermeable and the nicotine will migrate through the seal itself.

A cartridge 10 of the type described above can be used in conjunction with a mouthpiece 22 as shown in FIG. 2. By forming the cylindrical body 12 of Barex and using pieces of Barex-coated aluminum foil to form the passageway barrier portions, the nicotine free base charged into the reservoir 16 is prevented from migrating out of the cartridge 10 by inserting and maintaining the nicotine-containing reservoir 16 in an oxygen-free environment. For example, by charging the cartridge 10 with an inert gas such as nitrogen, degradation through interaction with oxygen of the nicotine free base is prevented. In this way, a fully effective dose of nicotine is available for the user upon penetration of the pieces of foil 18 as described below.

Alternatively to the construction described above, the nicotine-impermeable barrier can be formed in other ways. For example, the tube could be formed of PE or other types of rigid materials with a layer of Barex adhered to the inner surface of the tube. Instead of having a tube, a reservoir could be formed with openings in either end with the reservoir coated entirely with a layer of Barex with the ends being penetrable as discussed. Other suitable cartridges could also be formed in accordance with the invention as long as the nicotine is isolated from the atmosphere by means of a nicotine-impermeable barrier and the barrier is penetrable to release the nicotine when desired.

As shown in FIG. 2, a mouthpiece 22 can be used which includes a mouth engaging portion 24 and a cartridge holder 26. A passageway 28 is formed to extend from the mouth engaging portion 24 through to cartridge holder 26.

As shown in FIGS. 3A and 3B, in order to mount the cartridge 10 in the mouthpiece 22, the cartridge 10 is placed in the outer end of the cartridge holder 26, adjacent to a sharpened tip 30 which is formed around the portion of the passageway 28 that communicates with the cartridge holder 26. The sharpened tip 30 is in the form of a cylindrical section cut at an angle so that a cylindrical space 32 is formed between the outer surface of the sharpened tip and the inner surface of the cartridge holder 26 to receive a portion of the cylindrical body 12 as the cartridge 10 is pushed into place to the position shown in FIG. 3B in the direction of arrow 34.

The inner surface of the cartridge holder 26 and the cartridge 10 are designed so that when the cartridge 10 is in the position shown in FIG. 3B, the cartridge 10 is held in place by the cylindrical wall which forms the cartridge holder 26. By pushing the cartridge in the direction of the arrow 34, the pointed tip 30 operates to penetrate the aluminum foil layer 18 on the inner end of the cartridge 10 and expose it to the passageway 28 of the mouthpiece 22.

In order to allow air to flow through the cartridge 10 and pass by or through the reservoir 16, the nicotine-impermeable layer 18 on outer end of the cartridge 10 must also be penetrated. This can be done by any sharp object such as a knife or the like. However, one way of providing an easily-usable sharpened object is to provide dispensers 36A-B of the type shown in FIGS. 4A-B which are formed of molded plastic and contain a number of compartments 38A-B for receiving cartridges 10 (not shown). In FIG. 4A, a tray 40 is also provided for holding a mouthpiece 22. All of these components can be shrink wrapped in a transparent plastic and used as a sales package.

In order to provide a handy sharpened object for penetrating the foil layer 18 over the outer end of the cartridge 10, a sharpened tip 42A-B can be provided. In this way, after a cartridge 10 is inserted into the end of the mouthpiece 22 and pushed to the position shown in FIG. 3B, the outer end can be penetrated simply by pushing it against the sharpened tip 42A-B as shown, for example in FIG. 4A. In this way, the passageway 28 communicates with the atmosphere through the passageway 14 of the cartridge 10 so that the user can suck on the mouth engaging end 24 of the mouthpiece 22 in order to receive nicotine vapor as described.

An alternative to using a sharpened tip to penetrate either or both foil ends is to form the foil with a portion that can be grasped (not shown) and then having the user peel the foil layer 18 off the cartridge 10.

Another embodiment of the invention is shown in FIGS. 5 and 6 where a cartridge 10 of the same configuration described above is used in conjunction with a cartridge penetrator/cover 44. As shown in FIG. 5A, the penetrator/cover 44 is inserted over the outer end of the cartridge 10 and the combination is then inserted into the outer end of the cartridge holder 26 of the mouthpiece 22 similar to the one shown in FIGS. 2 and 3.

The cartridge penetrator/cover is formed of a cylinder 46 which defines a passageway 48, the outer end of which is defined by a cylindrical sharpened tip 50 which is similar in design to the sharpened tip 30 in the cartridge holder 26. An annular space 52 is formed between the outer surface of the sharpened tip 50 and the inner surface of the cylinder 46 for receiving the cylindrical body 12 of the cartridge 10.

After the penetrator/cover 44 is placed over the outer end of the cartridge 10, it is pushed toward the position shown in FIG. 5 in the direction of arrow 54 (FIG. 5B) so that the sharpened tip 50 operates to penetrate the foil layer 18 located over the outer end of the cartridge 10. In this way, the passageways 28 of the mouthpiece 22 and 14 of the cartridge 10 communicate with each other and with the atmosphere so that the user is able to suck on the mouthpiece and receive the nicotine vapor as described above.

The embodiment of the invention shown in FIGS. 5 and 6 can be packaged in a manner shown in FIG. 7 where a molded plastic tray 56 includes a number of compartments 58 designed to hold a cartridge and cartridge penetrator/cover 44 in the non-penetrating position shown in FIG. 5A. A compartment 60 can also be provided to hold a mouthpiece 22 with all of the elements being packaged by shrink wrapping them in transparent plastic (not shown).

By providing the inhaler described above, a cartridge for holding nicotine to be used in conjunction with the mouthpiece can be marketed without losing its effectiveness through an unnecessarily short shelf-life. By providing a cartridge with a nicotine-impermeable barrier, nicotine is prevented from migrating out of the cartridge and the dosage initially provided is maintained throughout the life of the product. Further, by maintaining and storing the nicotine reservoir in an oxygen-free atmosphere, the nicotine is prevented from degrading through the interaction with the oxygen and the effective level of the nicotine dose is maintained.

The foregoing description is not intended to be limiting in nature and the invention is intended to include all improvements and variations beyond those specifically described, which fall within the spirit and scope of the appended claims.

What is claimed is:

1. A nicotine delivery system with an extended shelf life, containing a measured amount of nicotine which can selectively be made accessible to a user, comprising:
    (a) a nicotine reservoir for holding and dispersing a measured amount of nicotine;
    (b) a self-sealed nicotine impermeable barrier formed as part of the nicotine reservoir, said barrier including at least one nicotine barrier layer formed essentially of a copolymer of acrylonitrile and methyl acrylate;
    (c) the barrier layer including at least two adjacent surfaces heat sealed to form a continuous nicotine impermeable barrier so that the nicotine can be prevented from migration outside the reservoir.

2. The system of claim 1, wherein the reservoir comprises a porous polymer plug charged with a solution including at least nicotine free-base.

3. The system of claim 1, wherein the barrier further includes a second barrier layer formed of metal foil adhered to at least a portion of the outer surface of the nicotine barrier layer.

4. The system of claim 3, wherein said metal foil is formed of aluminum foil.

5. The system of claim 1, wherein the nicotine reservoir is maintained in a gas inert to nicotine.

6. The system of claim 5, wherein said inert gas is nitrogen.

7. A method of preparing a nicotine delivery system with an extended shelf life, comprising the steps of:
    loading a nicotine reservoir with a measured amount of nicotine;
    introducing the loaded reservoir into a nicotine impermeable barrier layer formed essentially of a copolymer of acrylonitrile and methyl acrylate; the barrier layer including at least two adjacent surfaces;
    creating an oxygen free environment about the reservoir;
    heat sealing said adjacent surfaces to form a continuous nicotine barrier so that the reservoir is maintained in an effectively oxygen-free environment.

8. The method of claim 7, wherein the nicotine reservoir comprises a porous polymer plug charged with a solution including at least nicotine free-base.

9. The method of claim 7, wherein the step of loading further includes the steps of:
    introducing the nicotine reservoir into a chamber;
    creating an oxygen-free environment within said chamber;
    charging the reservoir with nicotine in said chamber; and
    removing said charged reservoir from said chamber in an oxygen-free environment.

10. The method of claim 9, wherein the step of creating an oxygen-free environment includes evacuating air from the chamber.

11. The method of claim 10, wherein the step of creating an oxygen-free environment includes charging the chamber with a gas inert to nicotine.

12. The method of claim 9, and further including the step of sealing the charged reservoir in an oxygen-free environment.

13. The method of claim 7, and further including the step of adhering a second barrier layer formed of metal foil to at least a portion of the outer surface of the nicotine barrier layer.

* * * * *

UNITED STATES PATENT AND TRADEMARK OFFICE
CERTIFICATE OF CORRECTION

PATENT NO. : 5,400,808
DATED : Mar. 28, 1995
INVENTOR(S) : James E. Turner, Michael P. Ellis, Ronald G. Oldham, Ira Hill, Bengt E. Malmborg, and Sven-Börje Andersson It is certified that error appears in the above-identified patent and that said Letters Patent is hereby corrected as shown below:

on the title page, left column, the section reading

[*] Notice: The portion of the term of this patent subsequent to Dec. 1, 2009 has been disclaimed.

should read

[*] Notice: The term of this patent shall not extend beyond the expiration date of U.S. Patent No. 5,167,242.

Signed and Sealed this

Thirty-first Day of March, 1998

Attest:

BRUCE LEHMAN

*Attesting Officer*      *Commissioner of Patents and Trademarks*